United States Patent [19]

Harman, III et al.

[11] Patent Number: 4,707,244
[45] Date of Patent: Nov. 17, 1987

[54] SOLID STATE SENSOR ELEMENT

[75] Inventors: John N. Harman, III, Placentia; Radhakrishna M. Neti, Brea, both of Calif.

[73] Assignee: Beckman Industrial Corporation, LaHabra, Calif.

[21] Appl. No.: 819,936

[22] Filed: Jan. 21, 1986

[51] Int. Cl.$^4$ ............................................. G01N 27/46
[52] U.S. Cl. .................................... 204/430; 204/1 T; 73/336.5; 73/336
[58] Field of Search ................. 204/1 W, 430; 73/335, 73/336, 336.5

[56] References Cited

U.S. PATENT DOCUMENTS

| | | | |
|---|---|---|---|
| 2,238,903 | 4/1941 | Lieneweg | 204/430 |
| 3,001,918 | 9/1961 | Czuha | 204/430 |
| 3,232,851 | 2/1966 | Haber et al. | 204/430 |
| 3,954,590 | 5/1976 | Czuha | 204/430 |
| 3,981,785 | 9/1976 | Sandler | 204/1 S |
| 4,280,885 | 7/1981 | Savery | 204/430 |
| 4,307,373 | 12/1981 | Johnston | 73/336.5 |
| 4,343,688 | 8/1982 | Harwood | 204/430 |

OTHER PUBLICATIONS

Clayton, "Moisture & Humidity, Measurement & Control in Science & Industry", pp. 535-544, ISA (1985).
Rochinsky, "Moisture & Humidity, Measurement & Control in Science & Industry", pp. 699-706, ISA (1985).

Primary Examiner—T. Tung
Attorney, Agent, or Firm—Plante Strauss Vanderburgh

[57] ABSTRACT

A solid state sensing element comprising a nonporous, structurally stable, electrically insulating substrate on which is disposed spaced apart pairs of electrodes for contact with moisture. A hygroscopic electrolytic material is located in close proximity to the electrodes as by coating the electrodes with the hygroscopic material. A catalyst is deposited in close proximity to the electrodes and is electrically insulated therefom. The electrodes are connected to a source of potential and current measuring instrumentation. Moisture is trapped by the hygroscopic material and electrolyzed at the electrodes. The catalyst recombines the hydrogen and oxygen thus formed to water so there is no net consumption of water by the element and equilibrium is established at the sensor surface and the atmosphere adjacent the sensor surface. Any change in partial pressure in the atmosphere adjacent the sensor surface is reflected by the movement of water molecules to the area of least concentration which produces a change in amount of moisture being electrolyzed and an increase or decrease in the current required by the element to electrolyze water.

31 Claims, 6 Drawing Figures

SOLID STATE SENSOR ELEMENT

FIELD OF THE INVENTION

This invention relates to solid state sensor elements and more particularly to solid state sensor elements for the determination of moisture.

BACKGROUND OF THE INVENTION

Various sensors for measuring the moisture content of a sample are known in the art. The various types of sensors are their basic principles of operation are described in a paper by Stanley Ronchinsky entitled "An Electrochemical Sensor for Trace Moisture in Gases," *Moisture and Humidity, Measurement and Control in Science and Industry*, 1985, pages 699 to 706. Of the different types of sensors described, the sensor type referred to as the "Electrolyzing Sensor" appears to be best suited for applications where continuous monitoring of moisture is required and for other industrial applications for the detection of trace amounts of moisture in samples.

Electrolytic sensors employ a moisture scavenger to trap the moisture in the sample and measure the amount of current required to electrolyze the trapped moisture. The operating principle of these sensors is Faraday's law of electrolysis in which the electrical charge required to electrolyze the water is the measure of the water content of the sample. Electrolysis is carried out by a pair or pairs of electrodes disposed in the body of the sensor.

The Keidel cell is an example of a moisture sensor operating on the electrolysis principle. Essentially the Keidel cell consists of a body which contains a pair of noble metal electrodes and which is packed with a suitable water scavenger such as phosphorous pentoxide. A sample stream is introduced into the body and the moisture is retained by the hygroscopic scavenger. The retained moisture is electrolyzed at the electrodes and the current required to electrolyze the moisture is measured. The Keidel cell and other forms of electrolytic sensors operating on the same principle require that the active area of the sensor be exposed to a constant flow of sample past the electrodes of the sensor. Variations in the sample flow rate can result in erroneous measurements and over time the hygroscopic scavenger tends to plug, causing a restriction in the flow of sample through the sensor, thus shortening the useful life of the sensor. An alternative to this is to introduce a known volume of sample into the sensor and measure the total current over time required to completely electrolyze the moisture in the known volume of sample. This is time consuming and does not lend itself to continuous monitoring. In addition, sensors of the type described have slow response times to changes in the moisture content of the sample and are not sensitive over a wide range of moisture content.

Accordingly, it would be highly desirable to provide a moisture sensor which retains the accuracy and reliability of the electrolytic sensors and which is sensitive over a wide range of moisture content. In addition, it would be desirable to provide a moisture sensor which measures the moisture content of a sample independent of the flow rate or volume of the sample to which the sensor is exposed, thus rendering the sensor more useful for the measurement of moisture contained in a solid as well as in a fluid.

SUMMARY OF THE INVENTION

In accordance with the present invention, there is provided a solid state sensor for the determination of moisture comprising at least a pair of inert, conductive electrodes disposed on a structurally stable, electrically insulating substrate for exposure to moisture, the electrodes being spaced apart to define an interelectrode gap therebetween. A hygroscopic electrolytic material is disposed in close proximity to the electrode surfaces and the electrodes are electrically connected to a source of electrical potential and current measuring instrumentation. A catalyst is disposed in close proximity to the electrodes and electrically insulated therefrom. Although not essential to the function of the sensor, in an embodiment of the invention a moisture permeable membrane may overlie the electrode carrying surface of the substrate and in certain other embodiments of the invention described hereinafter the membrane may include the hygroscopic electrolytic material, the catalyst or both.

In operation, water molecules contacting the hygroscopic electrolytic material are held thereby in close proximity to the electrodes. The water molecules are electrolyzed at the electrodes to hydrogen and oxygen. The hydrogen and oxygen thus formed recombine as water in the presence of the catalyst. An equilibrium condition is established between the active surface of the senscr and the atmosphere immediately adjacent the active surface of the sensor. The current required for the electrolysis remains steady since there is no consumption of water at the sensor. Any change in the moisture content adjacent the active surface of the sensor will immediately result in a disturbance of the equilibrium condition which will result in water molecules moving from the area of highest concentration to the area of least concentration to re-establish equilibrium. This produces an increase or decrease in the moisture content at the active surface of the sensor with a resultant change in the number of water molecules being electrolyzed at the electrodes. The current required to carry out electrolysis will likewise increase or decrease as the case may be. In accordance with Faraday's law of electrolysis, the current change is directly related to the change in the moisture content of the sample. The current will continue to change until equilibrium conditions are re-established. Since the electrolysis by-products are recombined to water molecules at the surface of the sensor, and there is not net consumption of water, the sensor of the invention does not require a continuous flow or known volume of sample in order to function properly.

In accordance with the present invention, the sensor so constructed retains the convenience and reliability of conventional electrolytic sensors while exhibiting high sensitivity and rapid response to changes in moisture content of the sample. It is unnecessary to carefully control the flow of sample past the sensor and inaccuracies due to variations in the sample flow rate are avoided. In addition, inaccuracies due to depletion of moisture in the area immediately adjacent the membrane surface are also avoided, since the sensor does not consume water during operation. By the same token, since the sensor of the invention does not require a continuous flow of sample to operate accurately, it is useful for the determination of moisture given off by solids and viscous fluids.

Other aspects and advantages of the invention will become apparent from the following detailed description taken in conjunction with the drawings, in which:

DETAILED DESCRIPTION OF THE INVENTION

Figure 1:
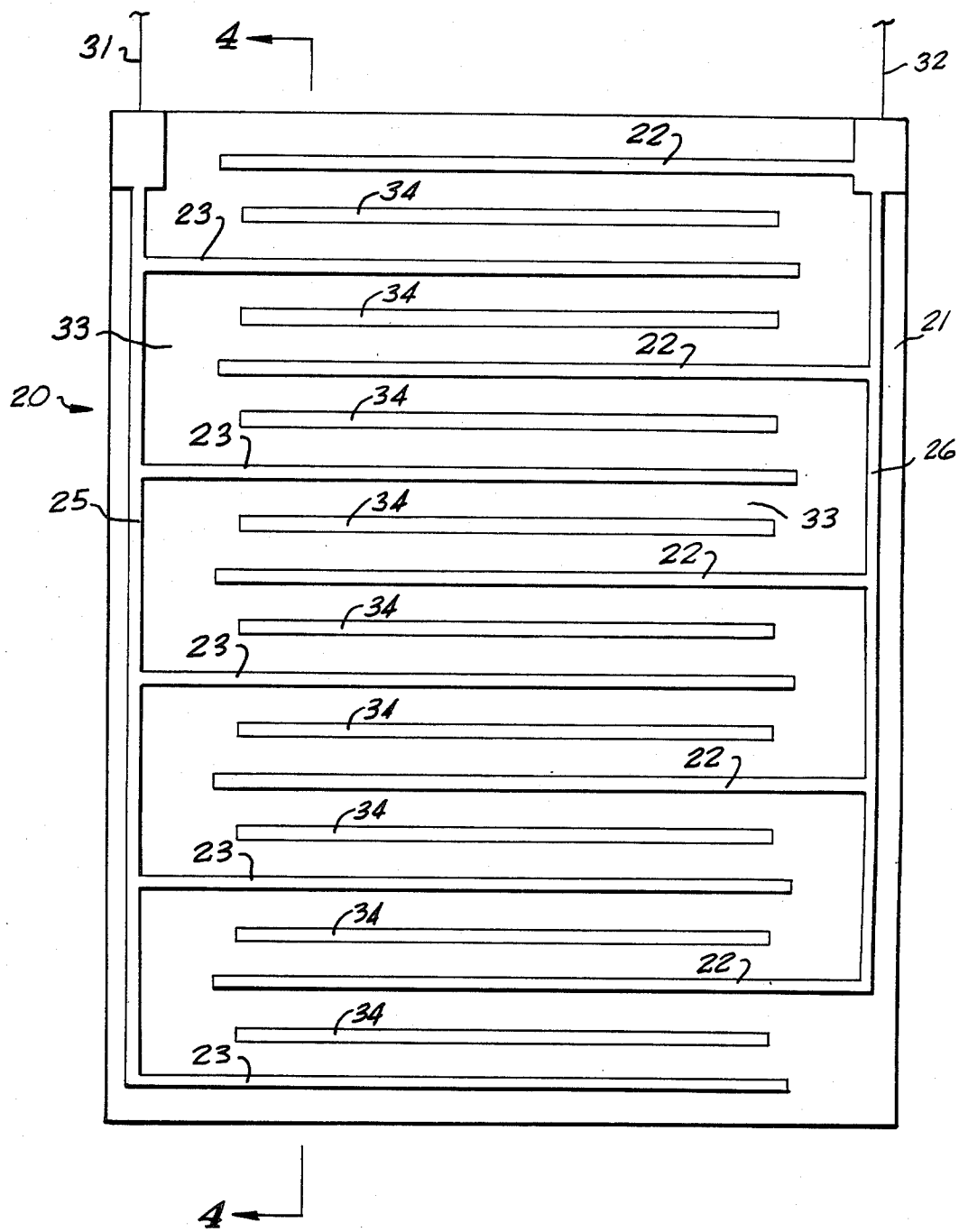
FIG. 1 is a plan view of a moisture sensing element constructed in accordance with the invention illustrating the electrodes arranged in an interdigitated pattern.

Referring to FIG. 1, there is shown a sensor, shown generally as 20, comprising a substantially planar substrate 21 on one face of which is deposited a plurality of conductive, substantially inert electrodes, 22, 23 arranged in an interdigitated pattern and series connected by conductors 25, 26 to contact points 28, 29 which in turn are connected by leads 31, 32 to a source of voltage and current measuring instrumentation, not shown. Each electrode 22 forms a pair with its adjacent electrode 23 and the electrodes are spaced apart to define a substantially uniform interelectrode gap 33 between electrodes. The interelectrode gap 33 may range from between about 0.002 inches and about 0.020 inches, depending upon the sensitivity required. The electrodes 22, 23 are deposited on the substrate 21 by known manufacturing techniques practiced for thick film and thin film depositions. For example, where the interelectrode gap 33 is small, i.e., on the order of 0.002 inches to about 0.010 inches, it is preferred to vacuum deposit the electrode material on the substrate 21, followed by a photoresist step to dilineate the closely spaced interdigitated electrode pattern. A line 34 of catalyst material or wire is deposited in the interelectrode gap 33 between electrodes 22, 23. The catalyst lines 34 are electrically insulated from the electrodes 22, 23 but are in close proximity to the electrodes in the interelectrode gap between each electrode pair.

Figure 2:
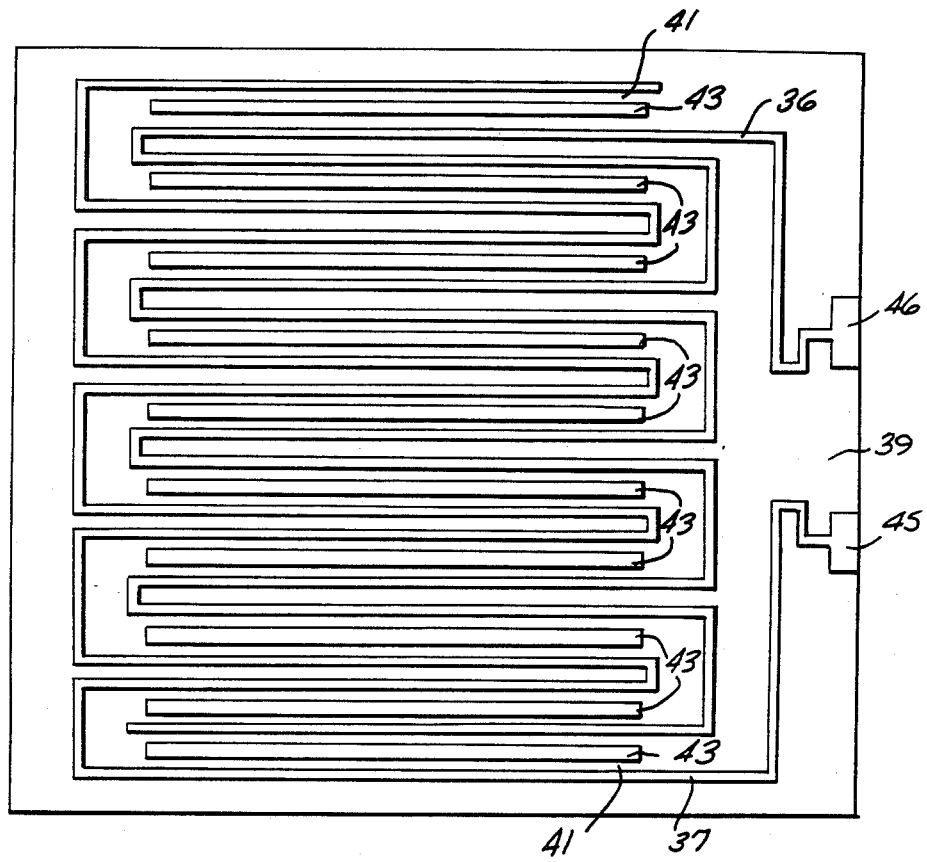
FIG. 2 is a plan view of another embodiment of the invention illustrating the electrodes arranged in a serpentine pattern.

Referring to FIG. 2, there is shown another embodiment of the invention in which a single electrode pair 36, 37 is deposited in a known manner on a substrate 39 in a serpentine pattern. The patterrn defines an interelectrode gap 41 between each leg thereof in which is deposited a line 43 of catalyst material. Contact points 45, 46 connect the electrodes 36, 37 to a source of potential and current measuring instrumentation, not shown.

Figure 3:
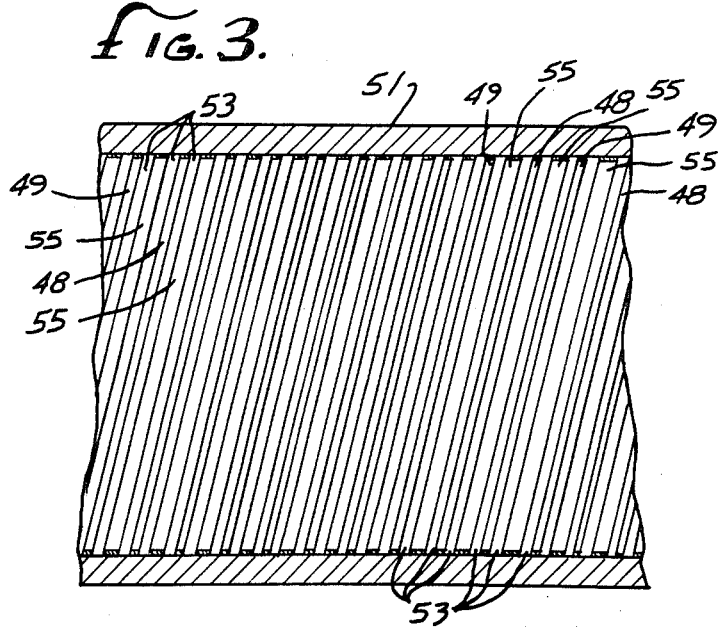
FIG. 3 is a plan view of another embodiment of the invention, partially broken away for purposes of illustration, illustrating a pair of electrodes helically wound within a tubular body.

Referring to FIG. 3, another embodiment of the invention is illustrated in which an electrode pair 48, 49 are wound within the bore of a tubular substrate 51 in a helical pattern. The windings are separated to provide an interelectrode gap 53 between electrodes 48, 49. The electrodes 48, 49 are electrically connected to a source of potential and current measuring instrumentation, not shown, by contact points, not shown. A winding 55 of catalyst material is disposed in the interelectrode gap 53 between the electrodes 48, 49 and the catalyst winding is electrically insulated from the electrodes.

While specific electrode patterns have been illustrated in FIGS. 1-3, the patterns may vary widely and are dependent on a number of design features such as, for example, the size and shape of the final assembly in which the sensor will be used, the desired sensitivity and the anticipated range of moisture content of the sample. Thus, for example, the electrodes may be deposited on the substrate in a circular pattern rather than the interdigitated or serpentine patterns illustrated or may be wound about a substrate core rather than within a tubular substrate body.

The substrate is formed from any nonporous, structurally stable, chemically inert, electrically insulating material. Such substrate materials include materials commonly used in the electronics field such as alumina, silicon, quartz and sapphire. In addition, certain polymeric materials, such as polyphenylene sulfide or the polyacrylics, exhibit the required properties of nonporosity structural stability, chemical inertness and electrical nonconductance to make them useful as substrate materials in the sensor of this invention. The substrate may comprise the sole base of the sensor or alternatively may be disposed as a layer over the surface of a base member of different material, such as stainless steel or aluminum.

The electrodes are composed of an electrically conductive, substantially inert material. The electrode material of choice is any of the noble metals since they are readily applied to the substrate by thick and thin film deposition techniques, are chemically inert and are excellent conductors.

The catalyst material is selected from materials which catalyze the reaction between hydrogen and oxygen to form water under conditions existing at the active surface of the sensor. Platinum and the oxides of platinum are highly suited for use as the catalyst material, as these materials are readily deposited on substrates and catalyze the reaction between hydrogen and oxygen at ambient temperature and pressure. The catalyst need not be deposited in the interelectrode gap between electrodes to achieve close proximity of the catalyst to the electrodes. Thus, as will be described in greater detail, the catalyst can be distributed in a water permeable membrane or deposited on an inert mesh overlying the active surface of the sensor in close proximity to the elec- trodes.

Figure 4:
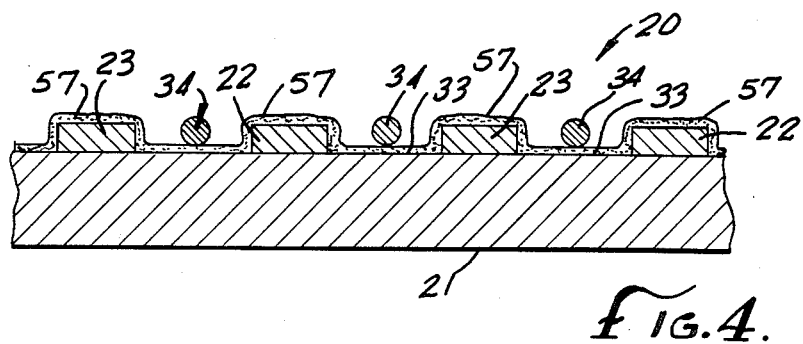
FIG. 4 is a cross-sectional view in enlarged scale and partially broken away for purposes of illustration, of the embodiment shown in FIG. 1 taken through line 4—4.

As is more clearly shown in FIG. 4, the exposed surfaces of the electrodes 22, 23 are provided with a coating 57 of a hygroscopic electrolytic material bridging the electrode, the purpose of which is to scavenge and trap moisture and serve as an electrolyte for electrolysis carried out at the electrodes. The preferred hygroscopic electrolytic material is phosphorous pentoxide, although certain polymeric materials such as polyimide polymers have also been found to have the desired electrolytic and water retention properties. In the preferred embodiment, the phosphorous pentoxide is applied over the electrodes 22, 23 by coating the surface of the sensor with an aqueous solution of phosphoric acid followed by drying the surface of the sensor element under dry nitrogen to convert the phosphoric acid to phosphorous pentoxide. The phosphorous pentoxide can also be coated on the surface by any other suitable method. For example, nitrogen is bubbled through a solution of trimethyl phosphite and the result is the saturation of the nitrogen gas with trimethyl phosphite vapor. The saturated nitrogen gas is admitted into a chamber in which is located the solid state chip and heated to temperatures in the range of 400°–600° F. Oxygen is also admitted into the chamber at the same time. The decomposition products of trimethyl phosphite at the high temperature in the presence of oxygen are uniformly deposited over the sensing element. Another method of deposition consists of depositing $P_2O_5$ from a solid ceramic source by what is generally known as chemical vapor deposition technique.

Figure 5:
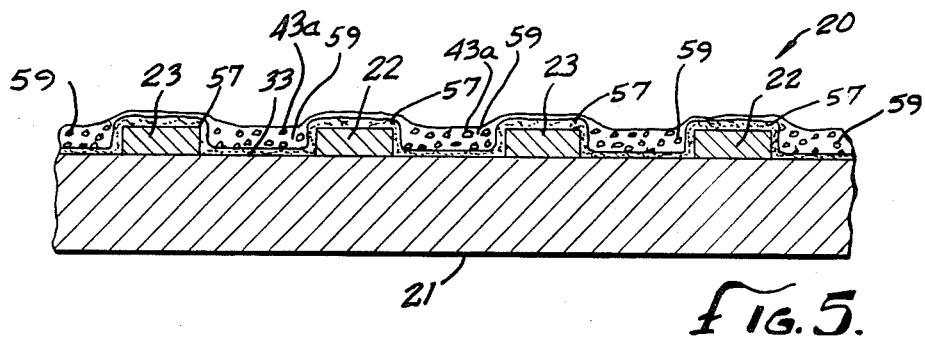
FIG. 5 is a cross-sectional view similar to FIG. 4 showing another embodiment of the invention.

As shown in FIG. 5, where like numbers designate like parts, the active surface of the sensor element 20 is provided with an outer thin membrane barrier 59 of an inert, moisture permeable material. The membrane barrier 59 is impervious to the components of the sample except water. Such materials are well known in the art and may include membrane materials selected from the group consisting of silicone, cellulose acetate and thermoplastic polytetrafluoroethylene. Although the membrane barrier may be deposited as a coating over the surface of the sensor element, such as the membrane coating 59 shown in FIG. 4, it may also be utilized as a separate element in a sensor assembly. In such cases it is desirable that the space between the membrane and the electrodes be minimized, since a substantial space between the electrodes and the membrane will result in a substantial increase in the response time of the sensor.

The operation of the sensor element 20 of the invention is most clearly described with reference to FIGS. 1 and 4. For purposes of example, the substrate 21 is sapphire, the electrodes 22, 23 are rhodium and the exposed surfaces of the electrodes are coated with a layer 57 of phosphorous pentoxide. A platinum wire is disposed in each of the interelectrode gaps 33 to serve as the catalyst 34.

A potential of at least 1.5 volts is imposed across the electrodes 22, 23. Moisture adjacent the surface of the sustrate 21 is scavenged by the hygroscopic layer 57 and electrolyzed to hydrogen and oxygen at the electrodes. The current required to carry out the electrolysis is a measure of the moisture concentration in accordance with Faraday's law of electrolysis. The hydrogen and oxygen produced at the electrodes 22, 23 recombine into water in the presence of the catalyst 34. The water so produced is again captured at layer 57 and the cycle is repeated. So long as the partial pressure of the moisture at the active surface of the sensor 20 is equal to the partial pressure of moisture in the atmosphere adjacent the active surface of the sensor 20, equilibrium is established with respect to moisture at the surface of the sensor and the atmosphere adjacent the surface of the sensor, since there is no net consumption of water. A change in the partial pressure in the atmosphere adjacent the surface of the sensor 20, such as an increase in the moisture content in a sample, causes a disturbance of the equilibrium conditions which results in the movement of water molecules to the area of least moisture concentration, i.e., lower partial pressure. In the case of an increase of partial pressure in the atmosphere adjacent the active surface of the sensor 20, water molecules move to the sensor surface where they are trapped by the hygroscopic layer 57 and then electrolyzed at the electrodes 22, 23. This produces an increase in the current needed to carry out the electrolysis. The current increase is directly related to the increased moisture content in the sample. Water molecules continue to move to the active surface of the sensor 20 until equilibrium conditions are re-established. A decrease in the partial pressure of moisture in the atmosphere adjacent the active surface of the sensor 20 produces a movement of water molecules away from the active surface of the sensor, resulting in less water being electrolyzed and producing a drop in current.

Under certain circumstances such as where it is desired to increase the range of moisture content measured by the sensor and where maximum sensitivity is not an essential requirement, a water permeable barrier may be disposed between the active surface of the sensor and the atmosphere adjacent the active surface of the sensor. The water permeable barrier may be a coating on the active surface of the sensor or may comprise a separate membrane element. Materials suitable for use as the moisture permeable barrier are known in the art and include materials such as silicone nylon, cellulose acetate, cellulose acetate butyrate and fluoroethylene polymers. A preferred material is an expanded polytetrafluoroethylene film having a pore size of about .01 micron to about 50 microns sold under the trademark GORE-TEX ® by W. L. Gore & Associates, Inc. Elkton, Maryland. The thickness of the barrier may range from about 0.05 microns to about 100 microns depending on the barrier material. It is preferred that the barrier thickness be about 2 microns in order to retain a high response time for the sensor element. Referring to FIG. 5, where like numbers indicate like elements, the sensor 20 comprises the substrate 21, on one surface of which are deposited electrodes 22, 23 which are coated by a layer 57 of hygroscopic electrolytic material. A moisture permeable barrier 59 is deposited as a coating over the active surface of the sensor 20.

As previously mentioned, the catalyst may be incorporated in the barrier layer 59 rather than in the interelectrode gap 33 between electrodes 22, 23. As shown in FIG. 5, the catalyst material is distributed in the barrier layer 59 as particles 43 on which are electrically insulated from and maintained in close proximity to the electrodes 22, 23 by the barrier layer. A barrier thickness on the order of several microns is sufficient to retain the catalyst in close proximity to and electrically insulated from the electrodes 22, 23 when the barrier is composed of expanded tetrafluoroethylene, although minimum thickness may vary using other materials to form the moisture permeable barrier 59, depending upon the dielectric constant of the material and its permeability to water.

Figure 6:
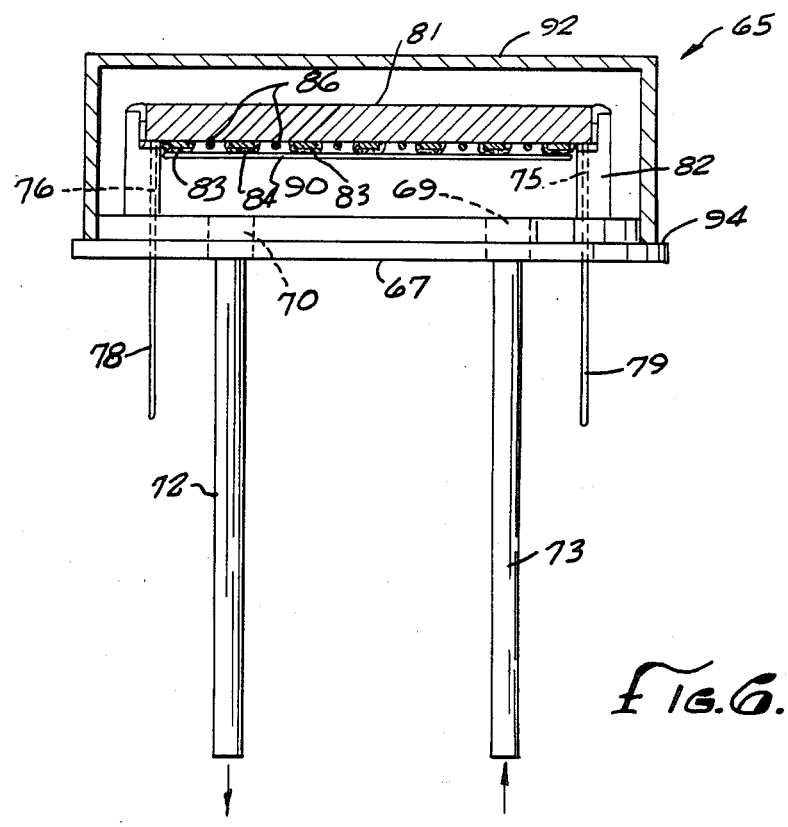
FIG. 6 is a side view, partially in section, illustrating a moisture sensing assembly including a sensor element constructed in accordance with the invention.

Referring to FIG. 6, there is illustrated as assembly employing the sensor element of the invention. The assembly, shown generally as 65, comprises a base member 67 provided with through-running passages 69, 70 which communicate with sample inlet tube 72 and sample outlet 73 respectively extending from the lower face of the base member. Openings 75, 76 are provided at the circumference of the base member in which are retained contact pins 78, 79 for mounting the assembly on a circuit board. A sensor element 81 with electrodes 83, 84 arranged in a serpentine pattern as illustrated in FIG. 2 is retained by mounting member 82 on the upper face of the base member 67. Platinum wires 86 are disposed in the interelectrode gaps 88 between the electrodes 83, 84 in the manner described for the embodiment shown in FIG. 2. A water permeable membrane 90 seals the electrodes 83, 84 and the catalyst platinum wires 86 from the sample. Membrane 90 is clamped by the mounting member 82. The assembly 65 is completed by a cap 92 which is retained on shoulder 94 formed at the periphery of the base member 67.

Sample flowing into the interior of the assembly 65 is prevented from reaching the sensor element 81 by the membrane 90. A change in the partial pressure of moisture at the exterior of the membrane 90 will disturb the equilibrium established between the interior and exterior of the membrane and water molecules will diffuse through the membrane to the side of least concentration and the sensor element responds to such change in the manner and according to the principles already described.

While various embodiments and modifications of the invention have been described in the foregoing description and illustrated in the drawings, it will be understood that minor changes may be made in the details of construction as well as in the combination and arrangement of parts without departing from the spirit and scope of the invention as claimed.

What is claimed is:

1. A solid state moisture sensing element comprising a non-porous, structurally stable, inert electrically insulating substrate having at least a pair of electrodes disposed on a surface thereof for exposure to moisture, said electrodes being spaced apart to define an interelectrode gap therebetween, a hygroscopic electrolytic material bridging said electrodes, means electrically connecting said electrodes to a source of electrical potential and current measuring instrumentation, the improvement comprising a catalyst material disposed in close proximity to said electrodes and electrically insulated therefrom for catalyzing the reaction between hydrogen and oxygen to form water.

2. The element of claim 1, wherein said hygroscopic electrolytic material is selected from the group consisting of phosphorous pentoxide and polyimide polymers.

3. The element of claim 1, wherein said electrodes are coated with said hygroscopic, electrolytic material.

4. The element of claim 1, wherein said catalyst element is selected from the group consisting of platinum and the oxides thereof.

5. The element of claim 1, wherein said inert, electrically insulating substrate is selected from the group consisting of silicon, quartz, alumina, sapphire, polyphenylene sulfide and polyacrylics.

6. The element of claim 1 further including a moisture permeable, chemically inert coating over said electrodes, said hygroscopic electrolytic material and said catalyst element.

7. The element of claim 6, wherein said coating is selected from the water permeable, chemically resistant group of polymeric materials consisting of silicone, nylon, cellulose acetate, cellulose acetate butyrate and expanded polytetrafluoroethylene.

8. The element of claim 6 wherein particles of said catalyst are disposed in said coating.

9. The element of claim 6 comprising particles of said hygroscopic electrolytic material disposed in said coating.

10. The element of claim 6 comprising particles of said hygroscopic electrolytic material and said catalyst disposed in said coating.

11. The element of claim 1, wherein said catalyst is disposed in the interelectrode gap between said electrodes.

12. The element of claim 1, wherein said electrodes are interdigitated one with the other.

13. The element of claim 1, wherein said electrodes are disposed on said substrate in a serpentine pattern.

14. The element of claim 1, wherein said electrodes are wound within the bore of a tubular substrate.

15. The element of claim 1, wherein said electrodes are wound about a substrate core.

16. The element of claim 1, wherein said electrodes are disposed on said substrate in a circular pattern.

17. The element of claim 1, wherein said electrodes are composed of a noble metal.

18. A sensor for the determination of moisture content of a sample comprising a substantially planar, chemically inert, structurally stable and electrically insulating substrate, elongated electrodes having surfaces for exposure to moisture deposited in an interdigitated pattern on one surface of said substrate and being supported thereby, said electrodes being spaced apart to define an interelectrode gap therebetween, hygroscopic electrolytic material bridging said electrode surfaces, and means electrically connecting said electrodes to a source of electrical potential and to current measuring means and catalyst material disposed in close proximity to said electrode surface and electrically insulated thereform whereby moisture is converted to hydrogen and oxygen by electrolysis at said electrodes and current required to effect the electrolysis is directly related to the moisture content at the electrode surface and the oxygen and hydrogen are recombined to water in the presence of said catalyst so that there is no net consumption of moisture by said sensor.

19. The sensor of claim 18 further including a moisture permeable, chemically inert both barrier disposed over the substant surface carrying said electrodes.

20. The sensor of claim 18, wherein particles of said catalyst material are contained in said barrier.

21. The sensor of claim 19, wherein particles of said hygroscopic, electrolytic material are contained in said barrier.

22. The sensor of claim 19, wherein said moisture permeable barrier is selected from the group of polymineric materials consisting of silicone nylon, cellulose acetate, cellulose acetate bytyrate and expanded polytetrafluoroethylene.

23. The sensor of claim 19, wherein said moisture permeable barrier is of expanded polytetrafluoroethylene having a pore size of between about 0.01 micron to about 50 microns.

24. The sensor of claim 18, wherein said catalyst material is deposited on said substrate in the interelectrode gap between said electrodes.

25. The sensor of claim 18, wherein said hygroscopic, electrolytic material is coated on the surfaces of said electrodes.

26. The sensor of claim 18, wherein said substrate is selected from the group consisting of silicon, quartz, alumina, sapphire, polyphenylene sulfide and polyacrylics.

27. The sensor of claim 18, wherein said substrate is sapphire.

28. The sensor of claim 18, wherein said hygroscopic electrolytic material is selected from the group consisting of phosphorous pentoxide and polyimid polymer.

29. The sensor of claim 18, wherein said hygroscopic electrolytic material is phosphorous pentoxide.

30. The sensor of claim 18, wherein said catalyst material is selected from the group consisting of platinum and the oxides thereof.

31. A moisture sensor assembly consisting of a base member and cap defining a hollow body, a solid state moisture sensing element disposed in the interior of said body, said element comprising a structurally stable, inert, electrically insulating substrate having a planar surface on which are disposed at least a pair of elongated electrodes, said electrodes being spaced apart to define a uniform interelectrode gap therebetween and catalyst material being disposed in said interelectrode gap and electrically insulated from said electrodes, a coating of hygroscopic electrolytic material bridging said electrodes, a moisture permeable membrane overlying said electrodes to provide a barrier between said electrodes and a fluid sample stream, means carried by said base for retaining said moisture sensing element and said membrane, means electrically connecting said electrodes to a source of potential and current measuring instrumentation, said body being provided with ingress and egress passages for the flow of a fluid sample stream past said membrane.

* * * * *

UNITED STATES PATENT AND TRADEMARK OFFICE
CERTIFICATE OF CORRECTION

PATENT NO. : 4,707,244
DATED : November 17, 1987
INVENTOR(S) : Harman, III et al.

It is certified that error appears in the above—identified patent and that said Letters Patent is hereby corrected as shown below:

In the claims:

Column 8, line 33, after inert, delete "both"

Signed and Sealed this

Fifth Day of April, 1988

Attest:

DONALD J. QUIGG

*Attesting Officer*     *Commissioner of Patents and Trademarks*